United States Patent [19]

Kilshaw, deceased et al.

[11] 4,123,768
[45] Oct. 31, 1978

[54] METHOD AND APPARATUS FOR PHOTOGRAPHICALLY RECORDING THREE-DIMENSIONAL MODELS OF DENTAL ARCH PROFILES

[75] Inventors: James Kilshaw, deceased, late of Leigh, England, by Edna M. Kilshaw, legal representative; Edward Dervin, Chadderton, England

[73] Assignee: Victoria University of Manchester, Manchester, England

[21] Appl. No.: 775,977

[22] Filed: Mar. 9, 1977

[51] Int. Cl.$^2$ .............................................. G03B 15/00
[52] U.S. Cl. ..................................... 354/292; 354/80
[58] Field of Search ................................ 354/75–77, 354/80, 81, 62, 293, 294, 290–292; 33/1 BB, 174 D, 174 P; 346/33 ME, 107 R

[56] References Cited

U.S. PATENT DOCUMENTS

| | | | |
|---|---|---|---|
| 2,163,125 | 6/1939 | Jeffreys et al. | 354/80 |
| 2,478,545 | 8/1949 | Pearce | 354/76 X |
| 2,599,269 | 6/1952 | Markle | 354/80 |
| 3,108,523 | 10/1963 | Nuchman et al. | 354/76 X |
| 3,898,683 | 8/1975 | Breads | 354/292 |

FOREIGN PATENT DOCUMENTS 861,972 3/1961 United Kingdom ................ 354/290

OTHER PUBLICATIONS

Taylor, B. L. & Bronson, J. F., *Photomacrography in Color as an Aid in Dental Caries Research*, in Dental Rad. & Photo. 23(1): pp. 10–12, 1950.

Gibson, H. L., *Photographing Dental Casts*, in Dental Rad. & Photo. 30(1): pp. 7–11, 1957.

*Primary Examiner*—John Gonzales
*Attorney, Agent, or Firm*—Hubbell, Cohen, Stiefel & Gross

[57] ABSTRACT

A method and apparatus for accurately photographically recording three-dimensional models of dental arch profiles in a plurality of photographic views taken in centric occlusion and in apposition. The method involves photographing such models in centric occlusion in a plurality of views obtained by rotating the model about an axis normal to the occlusal reference plane and lying in the mid-saggital plane substantially 15 mm. posterior of the inter-canine line. The apparatus comprises a supporting bench bearing a mounting platform for the model and a camera holder spaced from one another by a predetermined substantially constant distance. Means are further provided for rotating the mounting platform to facilitate exposure of the model in a plurality of views in centric occlusion, together with means for adjusting the location of the camera holder in the three mutually perpendicular directions, axially along the bench relative to the mounting platform, transversely across the longitudinal axis of the bench, and vertically of the mounting platform.

10 Claims, 11 Drawing Figures

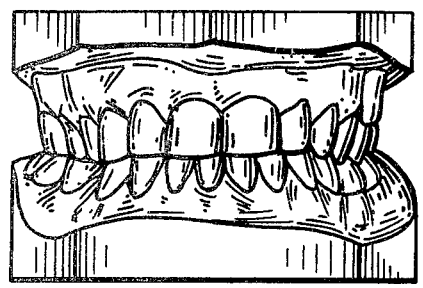
FIG. IA
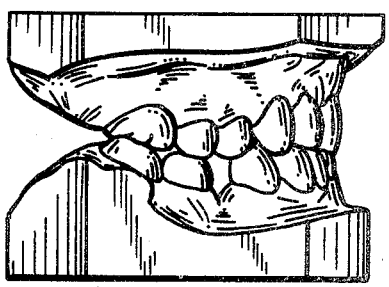
FIG. IB
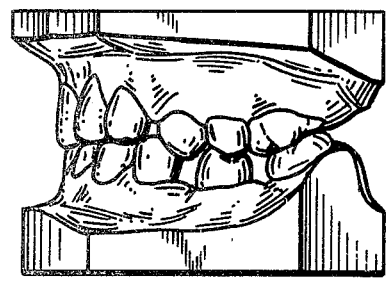
FIG. IC
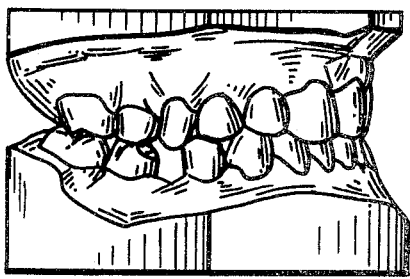
FIG. ID
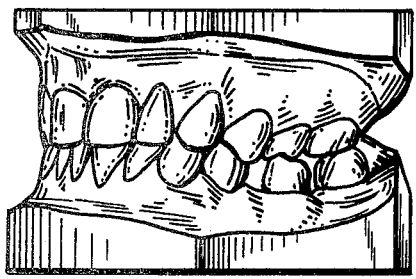
FIG. IE
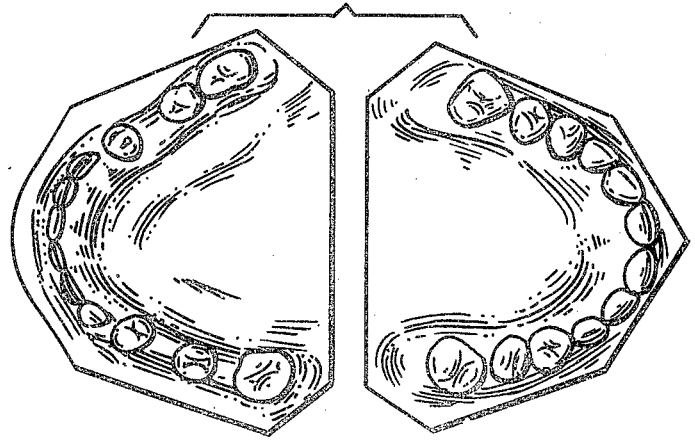
FIG. IF

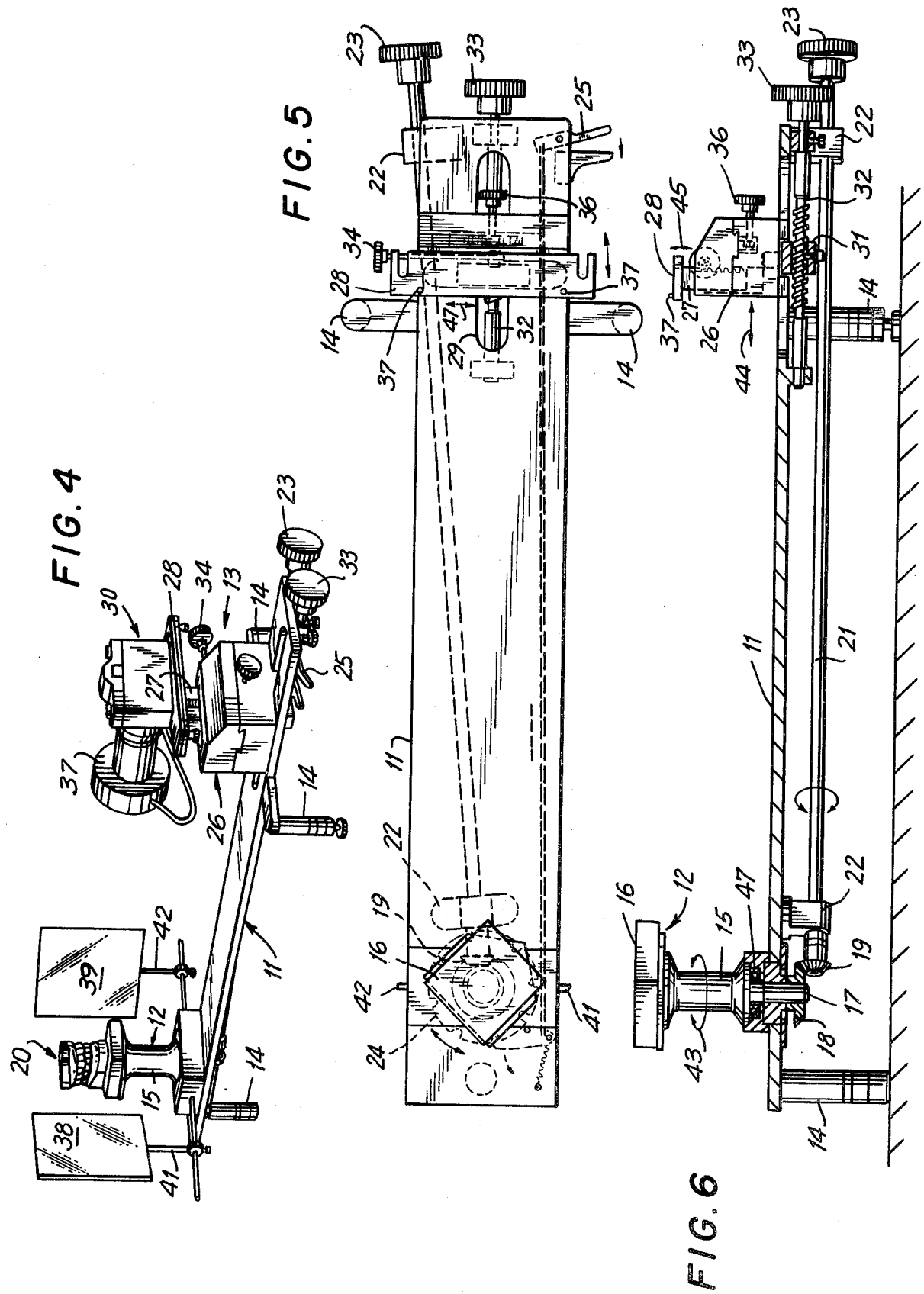

METHOD AND APPARATUS FOR PHOTOGRAPHICALLY RECORDING THREE-DIMENSIONAL MODELS OF DENTAL ARCH PROFILES

BACKGROUND OF THE INVENTION

This invention relates to a method and apparatus for the photographic measurement of dental models, and more particularly to a method and means for making an accurate photographic record of three-dimensional models of dental arch profiles free of substantial magnification errors.

A dental model is a cast, commonly made of gypsum, in the form of a facsimile of the dentition and/or dental arch in the mouth. The dental model is used for the study of dentition anomalies for the correction of defects of arch shape by extraction, and/or the mechanical correction of the teeth by braces or the like. It is also useful as a form for the production of such appliances, and for retaining information of any changes in the patient's dentition and/or dental arch which may take place over a considerable period of time.

The indexing and storage of these bulky and fragile models for long periods of time presents considerable difficulty, and additionally poses the real possibility of loss or irreparable damage. Thus, large numbers of dental models fill most of the available storage space in dental clinics or offices. Moreover, poor indexing and storage of the models often causes a considerable waste of professional man-hours searching for an elusive model which, if found, may well be damaged.

It is, accordingly, among the objects of the present invention to provide an improved technique, and an apparatus useful therein, for readily and accurately recording information respecting the configuration of a patient's dentition and/or dental arch, which technique is not subject to the various inconveniences and disadvantages inherent in the use of conventional three-dimensional dental models. The photographic recording procedure and apparatus described hereinafter provides just such an improved information storage and retrieval system.

SUMMARY OF THE INVENTION

In accordance with the present invention, a photographic method for accurately portraying a three-dimensional model of a dental profile in a plurality of two-dimensional photographic images has been provided. The method involves rotating the model about a point substantially 15 mm. e.g. from about 7 to 23 mm., from an origin defined by the intersection of the inter-canine line and the mid-saggital plane of the standard mean profile of the dental arch, and thereby sequentially photographing a plurality of views of the model in centric occlusion from a single distant point. It has been found that by rotating the model about the specified point, it is possible to maintain a substantially constant front conjugate distance between the model and the camera lens, and thereby produce a series of accurate two-dimensional images of the three-dimensional model at substantially constant magnification. Photographic records thus prepared may be readily stored, are not subject to substantial risk of damage, and may be readily retrieved. The photographic technique thus provides an effective substitute for three-dimensional models for dental profile records.

Further in accordance with the invention, a relatively simple apparatus is provided for carrying out the preceding method. Such apparatus comprises a supporting bench, a mounting platform thereon for supporting the dental model, and a camera holder on the bench and spaced longitudinally from the mounting platform for supporting a camera at a predetermined substantially constant, front conjugate distance from the model. Means are further provided for rotating the mounting platform to facilitate exposure of the model in the desired plurality of views in centric occlusion, and further means are provided for adjusting the location of the camera holder relative to the mounting platform in three mutually perpendicular directions, viz., axially along the bench, transversely across the longitudinal axis thereof, and vertically. Such apparatus may be readily employed, by even unskilled assistants, to accurately adjust and record the requisite photographic information characterizing the dental profile of any particular model.

Further details and modifications of the method and apparatus of the present invention will become apparent from consideration of the following detailed disclosure of preferred embodiments thereof, taken in connection with the accompanying drawings in which:

BRIEF DESCRIPTION OF THE DRAWINGS

FIG. 1 illustrates several views of a dental model which may be obtained by the photographic method of the present invention to fully characterize the dental profile thereof. The photographic record so obtained may thus include photographs of the model in centric occlusion in the anterior (FIG. 1A), the right and left oblique (FIGS. 1B and 1C) and the right and left lateral (FIGS. 1D and 1E) views, in addition to an occlusal view (FIG. 1F) of the top and bottom arches of the dental model in apposition;

FIG. 4 is a perspective view of a preferred embodiment of the apparatus of the invention;

FIG. 5 is a plan view, partially in section, of the apparatus of FIG. 4; and

FIG. 6 is an elevation, partially in section, of the apparatus of FIG. 4.

PREFERRED EMBODIMENTS OF THE INVENTION

Figure 2:
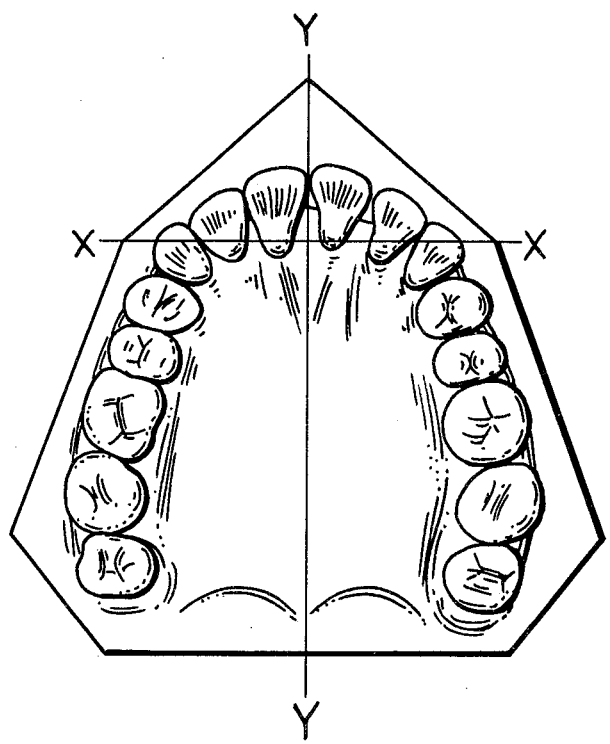
FIG. 2 is an illustration of the standard orthodontic trim of the dental model with the inter-canine line arbitrarily plotted as the X axis, and the mid-saggital plane arbitrarily plotted as the Y axis, thereon.

As indicated hereinabove, the method of the present invention involves the rotation of the dental model about a particular point designed to maintain a substantially constant front conjugate distance between the model and the lens of the camera recording the same. In this manner, the variation of magnification upon rotation of the profile into the desired views in centric occlusion may be minimized, as described more fully hereinafter. A standard set of photographs recording the information of a three-dimensional dental model may suitably comprise the anterior, lateral and oblique views in centric occlusion, and the top and bottom arch occlusal views of the dental model in apposition, as illustrated in FIG. 1 of the drawing. It will be understood that the present method may be utilized to provide accurate recording of any number of views of the dental model in centric occlusion, not merely the preferred standard views illustrated in FIGS. 1A–E. Whatever the number of individual views which may be desired, they are accurately obtained by the technique hereof.

The standard mean profile of the dental arch utilized for the determination of the point of rotation in accordance herewith was determined from a study of a number of dental models chosen with the widest possible anatomical variation (see Medical & Biological Illustration, 1976, 26, pages 219–222, the disclosure of which is incorporated by reference herein). The buccal crown circumference of the teeth was used to define the standard arch profile and such was plotted relative to the inter-canine line as the X axis and the mid-saggital plane as the Y axis. This arbitrary choice of axes conveniently fits the standard orthodontic trim of the dental model (FIG. 2).

The dental models photographically recorded by the present method are preferably prepared in the form of the standard orthodontic trim. It is, however, within the purview of this invention, and may at times be preferred, to utilize a modified model varying from the standard orthodontic trim to provide improved scale accuracy when it is desired to record occlusal views of the model in apposition. In such instance, it is preferred to trim the model of the upper arch in such a manner as to permit the parallel alignment of the upper trim of the model to the occlusal reference plane. This depth measurement is transferred in a similar manner to the model of the lower arch. By utilizing such procedure the two halves of the model are of identical thickness, resulting in the maintenance of constant scale in the photographic image and the prevention of image distortion. Any errors in the occlusal view are thus minimized, and limited to those of the dimensional stability of the photographic materials used.

Figure 3:
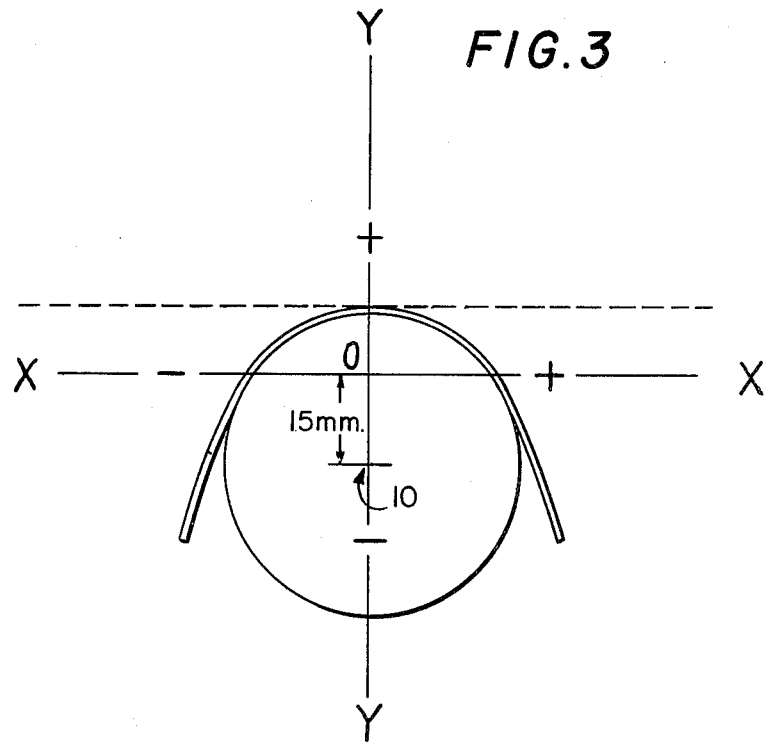
FIG. 3 is an illustration of the standard mean dental arch profile with the aforesaid coordinates plotted thereon together with the point of rotation of the dental model relative thereto, as determined in accordance with this invention.

As shown in FIG. 3, it has been shown that magnification errors can be minimized, if not totally eliminated, when the dental model is rotated about a point 10 substantially 15 mm., e.g. from about 7 to 23 mm., posterior from the origin 0 defined by the intersection of the inter-canine line and the mid-saggital plane. When the model is rotated about such a point it is possible to maintain a substantially constant front conjugate distance between the model and the camera for each of the desired photographic views, and thereby maintain substantially constant image magnification therein. Errors in magnification for different views in centric occlusion are thus generally maintained at within ±2%. In the case of even the maximum anatomical variation of the dental model from the standard mean dental arch profile illustrated in FIG. 3, it has been found that the maximum error in magnification is still less than 5% when rotated about the appropriate center 7 – 23 mm from the origin defined by the intersection of the inter-canine line and the mid-saggital plane. The magnification errors referred to herein are based on a 35 mm photographic format utilising a lens of focal length $f = 105$ mm and an object-lens distance of 525 mm. (See Medical and Biological Illustration, 1976, 26 pages 219–222). The limits in the positioning of the model relative to the camera are more critical if a lens of a shorter focal length is used or if the object-lens distance is shortened.

The photographic recording method hereof may be readily and efficiently carried out employing the preferred form of apparatus illustrated in FIGS. 4 – 6. As shown therein, the recording device comprises an optical or photographic bench 11 supporting, axially thereof, a mounting platform 12 for the dental model 20 and a camera holder 13 for a camera 30 (shown only in FIG. 4). The mounting platform and camera holder are both secured to the bench and spaced longitudinally from one another to facilitate photographic exposure of the model from any desired view in centric occlusion at a predetermined, substantially constant front conjugate distance, or for exposing the top and bottom arches in apposition.

As shown, the supporting bench 11 is suitably mounted horizontally on a plurality of leveling feet 14, which may be adjusted as desired.

The mounting platform 12 and camera holder 13 are so mounted that controlled relative movement may be achieved therebetween. Referring first to the mounting platform, such comprises a supporting pillar 15 carrying an upper, horizontally disposed platform 16. The platform may suitably be made of a lightweight plastic material or metallic alloy, and may be engraved to facilitate rapid and accurate positioning of the dental model thereon. The platform may be calibrated, e.g., at 5° intervals, to facilitate exposure of any number of intermediate, regularly angularly displaced views.

Pillar 15 is journaled for rotation on shaft 17 in bearing 47, which shaft may be rotated by means of bevel gears 18 and 19. Bevel gear 19 is mounted on control rod 21 which is mounted on bench 11 by standards 22. The control rod bears a control knob 23 on its remote end adjacent the end of the bench 11 and remote from the mounting platform 12. The control knob may be utilized to turn bevel gears 19 and 18, respectively, and thus rotate the mounting platform (in the direction of arrow 43 in FIG. 6) to photograph any desired view of the dental model.

Ratchet mechanism 24 (illustrated solely in FIG. 5 for clarity) actuated by lever 25 is further provided for pivoting mounting platform 12 into a number of predetermined positions, preferably the standard positions in which the dental model may be photographed in centric occlusion in the anterior, lateral and oblique views illustrated in FIG. 1. It will, however, be understood that the ratchet mechanism may be indexed to pivot the mounting platform into any desired number of positions.

The camera holder 13 is similarly mounted for movement relative to the mounting platform for the dental model. Thus, the camera holder comprises a mounting block 26 receiving pedestal 27 supporting a camera base plate 28. The mounting block is disposed above a slot 29 in bench 11 and incorporates a depending element 31 engaged by a threaded control rod 32. The latter extends longitudinally of the bench and has a control knob 33 secured thereto at its remote end adjacent the camera holder. Rotation of control knob 33 effects movement of mounting block 26, and hence the camera holder 13, axially of bench 11 by means of the threaded engagement of elements 31 and 32.

In similar manner, pedestal 27 is threadedly engaged with a gear and rack mechanism actuated by an adjustment knob 34. Rotation of such knob effects vertical displacement of pedestal 27, camera base plate 28 and of course, the camera 30 which may be mounted thereon (see FIG. 4).

Finally, a similar gear and rack mechanism actuated by a further control knob 36 is provided for effecting lateral movement of camera holder 13 and camera 30 transversely across the longitudinal axis of bench 11.

Control knobs 33, 34 and 36 thus adjust the position of the camera holder in three mutually perpendicular directions, axially along bench 11 (as indicated by arrow 44 in FIG. 6), vertically with respect thereto (as indicated by arrow 45 in FIG. 6), and transversely across the longitudinal axis thereof (as indicated by arrow 46 in FIG. 5). In this manner, the position of the camera holder (and hence the camera) may be regulated at will relative to the dental model to be photographed.

Camera 30 is mounted to base plate 28 on the camera holder, as by a number of locating pins 37. The camera as thus mounted may be disposed in any particular position relative to the mounting platform and the dental model to be photographed, and may be maintained at a predetermined substantially constant front conjugate distance from the model, as aforesaid. When it is desired to photograph a view of the top and bottom arches of the dental model in apposition, the model may be vertically mounted to a suitable plate, and the plate mounted to bench 11 adjacent mounting platform 12; alternatively, other means for supporting the model for exposure of an occlusal view thereof will be apparent to those skilled in the art.

Depending upon the type of camera and the particular focal length of the lens, the bench 11 may be varied in size or slats inserted therein to permit the camera apparatus to approach the model or alternatively to permit the model holder to approach the camera.

Referring now to FIG. 4, it is further desirable to provide a simple, standard and effective method of illuminating the model by means of a source of illumination fixably disposed at a constant distance from the model. One preferred illuminating means found suitable for this purpose comprises an electronic ring flash unit 37 mounted peripherally about the lens of camera 30. Desirably, the sides of the dental model are further illuminated from flash unit 37 by means of suitable reflectors 38 and 39, pivotally mounted adjacent mounting platform 12 on which the model is disposed. The reflectors are preferably of unpolished aluminum and are desirably mounted to adjustable rods 41 and 42, whose length or orientation may be modified as desired to provide any predetermined light effect.

It will be seen from the preceding that there is provided, in accordance with the present invention, a photographic recording method and apparatus which may be efficiently utilized for recording the complete configuration of a dental model. Such method, and the preferred apparatus utilized therefor, provide a convenient way of obtaining, storing and retrieving the information from three-dimensional dental models.

It will be understood that various changes may be made in the preferred embodiments of the method and apparatus hereof without departing from the scope of the present invention. Accordingly, the preceding description should be construed as illustrative and not in a limiting sense.

What is claimed is:

1. A method for the preparation of an accurate photographic record of a three-dimensional model of a dental arch profile, which comprises:
    (a) disposing models of the top and bottom arches of the dental arch profile in centric occlusion with the line of intersection of the mid-saggital plane and the occlusal reference plane of the models coincident with the axis of the lens of the recording camera and the anterior of the models facing the camera at a fixed model-lens distance;
    (b) rotating the models about an axis normal to the occlusal reference plane and lying in the mid-saggital plane from 7 to 23 mm. posterior of the inter-canine line; and
    (c) photographing a plurality of rotational views of the models to produce a series of accurate two-dimensional images of the dental arch profile at constant magnification.

2. The method of claim 1, in which the models are photographed in the anterior and both of the lateral and oblique views to accurately record the dental arch profile of the model in centric occlusion.

3. The method of claim 1, wherein the models are rotated about an axis 15 mm. posterior of the inter-canine line.

4. The method of claim 1, wherein the photographic record of the model is completed by exposure of an occlusal view of the top and bottom arches of the model in apposition.

5. The method of claim 1, wherein the models of the top and bottom arches are trimmed, prior to photographic exposure, so that the base of each is parallel to its occlusal reference plane and each said base is equally displaced from said reference plane to thereby establish a uniform model thickness and prevent image distortion upon the sequential exposures thereof.

6. An apparatus for the accurate photographic recording of a three-dimensional model of a dental arch profile, which comprises:
    (a) a supporting bench;
    (b) a mounting platform rotatably secured perpendicular to the bench, for supporting the models of the top and bottom arches of the dental arch profile in centric occlusion with the line of intersection of the mid-saggital plane and the occlusal reference plane of the models coincident with the axis of the lens of a recording camera and the anterior of the models facing the camera at a fixed model-lens distance;
    (c) means for rotating the mounting platform to rotate the models about an axis normal to the occlusal reference plane and lying in the mid-saggital plane from 7 to 23 mm. posterior of the inter-canine line;
    (d) a camera holder axially slidably secured to the bench and spaced longitudinally from the mounting platform for supporting a camera, said holder including a camera base plate which is formed for mounting the camera, a pedestal supporting the camera base plate, a mounting block which vertically slidably receives the pedestal, and means for vertical adjustment of the pedestal, said mounting block including means for transverse adjustment of the pedestal and being axially slidably secured to the bench; and
    (e) means for axial adjustment of the camera holder along the bench so that said camera may be placed at a predetermined, substantially constant distance from said models.

7. The apparatus of claim 6, wherein the means for rotating the mounting platform includes ratchet means for pivoting into at least five discrete positions to facilitate exposure of the model in centric occlusion in the anterior, and in both of the lateral and oblique views of the dental arch profile thereof.

8. The apparatus of claim 6, further including ring means for illuminating the model disposed axially of the camera lens, and reflector means disposed adjacent the mounting platform for pivotal movement relative thereto to effect the desired illumination thereof.

9. The apparatus of claim 6, wherein the means for rotating the mounting platform comprises a first, geared rotating means for rotating the platform into any desired position and a second rotating means incorporating a ratchet mechanism for displacing the platform into at least predetermined positions facilitating exposure of the model in centric occlusion in the anterior, and in both of the lateral and oblique views of the dental arch profile thereof.

10. The apparatus of claim 6, wherein the means for vertical adjustment of the pedestal comprises a gear and rack mechanism connecting the pedestal to the mounting block for vertically moving the pedestal relative to the mounting block, wherein the means for transverse adjustment of the pedestal comprises a transversely slidable joint within the mounting block interconnected by a gear and rack mechanism for moving the pedestal transverse of the bench, and wherein the means for axial adjustment of the camera holder comprises a screw thread mechanism connecting the mounting block to the bench for displacing the mounting block axially of the supporting bench.

* * * * *